United States Patent [19]

Lincoln

[11] 4,235,997

[45] Nov. 25, 1980

[54] 6-ALKOXY-ω-ARYL-PGI$_1$ COMPOUNDS

[75] Inventor: Frank H. Lincoln, Portage, Mich.

[73] Assignee: The Upjohn Company, Kalamazoo, Mich.

[21] Appl. No.: 70,951

[22] Filed: Aug. 30, 1979

Related U.S. Application Data

[62] Division of Ser. No. 892,108, Mar. 31, 1978.

[51] Int. Cl.$^3$ .......................................... C07D 307/935
[52] U.S. Cl. .............................. 542/426; 260/346.22; 260/346.73; 542/429
[58] Field of Search ...................... 260/346.22, 346.73; 542/426, 429

[56] References Cited

PUBLICATIONS

Johnson et al., J. Am. Chem. Soc. 99, 4182, (1977).

Primary Examiner—Henry R. Jiles
Assistant Examiner—Bernard Dentz
Attorney, Agent, or Firm—Robert A. Armitage

[57] ABSTRACT

Prostacyclin I$_1$ (PGI$_1$) derivatives and analogs having a 6-alkoxy feature and having pharmacological activity and processes for preparing them are disclosed.

13 Claims, No Drawings

6-ALKOXY-ω-ARYL-PGI₁ COMPOUNDS

DESCRIPTION

CROSS REFERENCE TO RELATED APPLICATIONS

This application is a divisional application of Ser. No. 892,108, filed Mar. 31, 1978, now pending.

BACKGROUND OF THE INVENTION

The present invention relates to novel 6-alkoxy-ω-aryl-PGI₁ compounds, useful as pharmaceutical agents, principally for the induction of certain prostacyclin-like pharmacological effects. The essential material consisting of description of the preparation and use of these substances is incorporated here by reference from Ser. No. 892,108, filed Mar. 31, 1978, now pending.

SUMMARY OF THE INVENTION

The present invention particularly relates to a compound of formula 1.

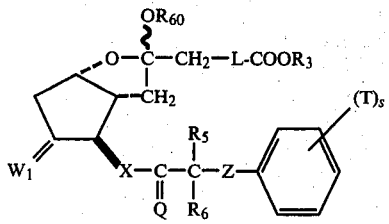

wherein L is
(1) $-(CH_2)_d-C(R_2)_2-$,
(2) $-CH_2-O-CH_2-Y-$, or
(3) $-CH_2CH=CH-$,
wherein d is zero to 5, $R_2$ is hydrogen, methyl or fluoro, being the same or different with the proviso that one $R_2$ is not methyl when the other is fluoro, and Y is a valence bond, $-CH_2-$, or $-(CH_2)_2-$;
wherein Q is oxo, $\alpha$-H:$\beta$-H, $\alpha$-R$_8$:$\beta$-OH, or $\alpha$-OH:$\beta$-R$_8$, wherein $R_8$ is hydrogen or alkyl of one to 4 carbon atoms, inclusive;
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa $(-O-)$;
   wherein Z represents an oxa atom $(-O-)$ or $C_jH_{2j}$ wherein $C_jH_{2j}$ is a valence bond or alkylene of one to 9 carbon atoms, inclusive, with one to 6 carbon atoms, inclusive between $CR_5R_6-$ and the (Ph);
   wherein T is alkyl of one to 4 carbon atoms, inclusive, fluoro, chloro, trifluoromethyl, or $-OR_7$ wherein $R_7$ is alkyl of one to 4 carbon atoms, inclusive, and s is zero, one, 2 or 3, with the proviso that not more than two T's are other than alkyl and when s is 2 or 3 the T's are either the same or different;
wherein $W_1$ is $\alpha$-OH:$\beta$-H, $\alpha$-H:$\beta$-OH, oxo, methylene, $\alpha$-H:$\beta$-H, or $\alpha$-CH$_2$OH:$\beta$-H;
wherein $R_{60}$ is straight-chain alkyl of one to 6 carbon atoms, inclusive; and
wherein X is
(1) trans$-CH=CH-$,
(2) cis$-CH=CH-$,
(3) $-C\equiv C-$, or
(4) $-CH_2CH_2-$;
wherein $R_3$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2 or 3 chloro or alkyl of one to 4 carbon atoms, inclusive;
(f) p-[(p-acetamido)benzamido]phenyl,
(g) p-(benzamido)phenyl,
(h) p-(acetamido)phenyl,
(i) $-(p-Ph)-NH-CO-NH_2$, wherein (p-Ph) is para-phenyl,
(j) $-(p(Ph))-CH=N-NH-C=O-NH_2$, wherein (p-Ph) is as defined above,
(k) $\beta$-naphthyl,
(l) $-CH(R_{11})-CO-R_{10}$
wherein $R_{10}$ is phenyl, p-bromophenyl, p-biphenylyl, p-nitrophenyl, p-benzamidophenyl, or 2-naphthyl; wherein $R_{11}$ is hydrogen or benzoyl;
(m) hydrogen; or
(n) a pharmacologically acceptable cation.

With regard to the divalent substituents described above, e.g., Q and $W_1$, these divalent radicals are defind as $\alpha$-R$_i$:$\beta$-R$_j$ where $R_i$ represents a substituent of the divalent moiety of the alpha configuration with respect to the cyclopentane ring and $R_j$ represents a substituent of the divalent moiety of the beta configuration with respect to the cyclopentane ring. Accordingly, when Q is defined as $\alpha$-OH:$\beta$-R$_8$, the hydroxy of the Q moiety is in the alpha configuration, i.e. as in prostacyclin, and the $R_8$ substituent is in the beta configuration. Not all carbon atoms to which such divalent moieties are attached represent asymmetric centers. For example, when both valence bonds are to hydrogen, (e.g., $W_1$ or Q is $\alpha$-H:$\beta$-H), then no asymmetric center is present.

DESCRIPTION OF THE PREFERRED EMBODIMENTS

The present invention particularly relates to the following chemical compounds:
9-Deoxy-6ξ,9α-epoxy-6ξ-methoxy-16-phenoxy-17,18,19,20-tetranor-PGF₁, methyl ester,
9-Deoxy-6ξ,9α-epoxy-6ξ-methoxy-16-phenoxy-17,19,19,20-tetranor-PGF₁, sodium salt.

I claim:
1. A compound of the formula

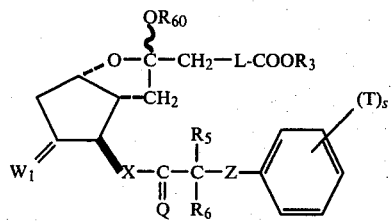

wherein L is
(1) $-(CH_2)_d-C(R_2)_2-$,
(2) $-CH_2-O-CH_2-Y-$, or
(3) $-CH_2CH=CH-$,
wherein d is zero to 5, $R_2$ is hydrogen, methyl or fluoro, being the same or different with the proviso that one $R_2$ is not methyl when the other is fluoro, and Y is a valence bond, $-CH_2-$, or $-(CH_2)_2-$;

wherein Q is oxo, α-H:β-H, α-R$_8$:β-OH, or α-OH:β-R$_8$, wherein R$_8$ is hydrogen or alkyl of one to 4 carbon atoms, inclusive;

wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (Ph);

wherein T is alkyl of one to 4 carbon atoms, inclusive, fluoro, chloro, trifluoromethyl, or —OR$_7$ wherein R$_7$ is alkyl of one to 4 carbon atoms, inclusive; and wherein s is zero, one, 2 or 3, with the proviso that not more than two T's are other than alkyl and when s is 2 or 3 the T's are either the same or different;

wherein W$_1$ is α-OH:β-H, α-H:β-OH, oxo, methylene, α-H:β-H, or α-CH$_2$OH:β-H;

wherein R$_{60}$ is straight-chain alkyl of one to 6 carbon atoms, inclusive; and wherein X is
 (1) trans—CH=CH—,
 (2) cis—CH=CH—,
 (3) —C≡C—, or
 (4) —CH$_2$CH$_2$—;

wherein R$_3$ is
 (a) alkyl of one to 12 carbon atoms, inclusive,
 (b) cycloalkyl of 3 to 10 carbon atoms, inclusive,
 (c) aralkyl of 7 to 12 carbon atoms, inclusive,
 (d) phenyl,
 (e) phenyl substituted with one, 2 or 3 chloro or alkyl of one to 4 carbon atoms, inclusive;
 (f) p-[(p-acetamido)benzamido]phenyl,
 (g) p-(benzamido)phenyl,
 (h) p-(acetamido)phenyl,
 (i) —(p-Ph)—NH—CO—NH$_2$, wherein (p-Ph) is para-phenyl,
 (j) —(p-Ph)—CH=N—NH—C=O—NH$_2$, wherein (p-Ph) is as defined above,
 (k) β-naphthyl,
 (l) —CH(R$_{11}$)—CO—R$_{10}$
wherein R$_{10}$ is phenyl, p-bromophenyl, p-biphenylyl, p-nitrophenyl, p-benzamidophenyl, or 2-naphthyl; wherein R$_{11}$ is hydrogen or benzoyl;
 (m) hydrogen; or
 (n) a pharmacologically acceptable cation.

2. A compound according to claim 1 wherein W$_1$ is α-OH:β-H and L is —(CH$_2$)$_3$.

3. A compound according to claim 2 wherein X is trans—CH=CH—.

4. A compound according to claim 3 wherein Q is α-OH:β-H.

5. A compound according to claim 4 wherein Z is oxa.

6. A compound according to claim 5 wherein R$_5$ and R$_6$ are hydrogen and R$_3$ is hydrogen, methyl or a pharmacologically acceptable cation.

7. 9-Deoxy-6ξ,9α-epoxy-6ξ-methoxy-16-phenoxy-17,18,19,20-tetranor-PGF$_1$, methyl ester, a compound according to claim 6.

8. 9-Deoxy-6ξ,9α-epoxy-6ξ-methoxy-16-phenoxy-17,18,19,20-tetranor-PGF$_1$, sodium salt, a compound according to claim 6.

9. A compound according to claim 5 wherein R$_3$, R$_5$ and R$_6$ are methyl.

10. A compound according to claim 4 wherein Z is methylene.

11. A compound according to claim 3 wherein Q is α-OH:β-CH$_3$.

12. A compound according to claim 2 wherein X is —CH$_2$CH$_2$—.

13. A compound according to claim 1 wherein W$_1$ is α-H:β-H and L is —(CH$_2$)$_3$—.

* * * * *

UNITED STATES PATENT OFFICE
CERTIFICATE OF CORRECTION

Patent No. 4,235,997           Dated    25 November 1980

Inventor(s)   Frank H. Lincoln

It is certified that error appears in the above-identified patent and that said Letters Patent are hereby corrected as shown below:

In Related U.S. Application Data: -- now U.S. Patent 4,207,242 --.

Column 1, line 9, "now pending" should read -- now U.S. Patent 4,207,242 --;

Column 4, line 13, "-$(CH_2)_3$" should read -- -$(CH_2)_3$- --.

Signed and Sealed this

*Seventh* Day of *April 1981*

[SEAL]

*Attest:*

RENE D. TEGTMEYER

*Attesting Officer*    *Acting Commissioner of Patents and Trademarks*